(12) United States Patent
Cai et al.

(10) Patent No.: US 6,460,412 B1
(45) Date of Patent: Oct. 8, 2002

(54) DETECTION OF DYNAMIC FLUIDIZED BED LEVEL IN A FLUIDIZED BED POLYMERIZATION REACTOR USING ULTRASONIC WAVES OR MICROWAVES

(75) Inventors: Ping Cai, Hurricane, WV (US); Kiu Hee Lee, So. Charleston, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 36 days.

(21) Appl. No.: 09/698,425

(22) Filed: Oct. 27, 2000

(51) Int. Cl.⁷ .................... G01F 23/00; G01H 5/00; G01N 29/00
(52) U.S. Cl. ................ 73/290; 73/597; 73/628
(58) Field of Search .................... 73/597, 602, 628, 73/629, 7, 290 V, 598; 250/357.1

(56) References Cited

U.S. PATENT DOCUMENTS

| | | | | |
|---|---|---|---|---|
| 4,470,299 A | * | 9/1984 | Soltz | 73/290 V |
| 4,770,038 A | * | 9/1988 | Zuckerwar et al. | 73/290 V |
| 4,831,565 A | | 5/1989 | Woodward | 364/571.01 |
| 4,858,144 A | * | 8/1989 | Marsaly et al. | 364/496 |
| 4,973,386 A | | 11/1990 | Callegari et al. | 201/1 |
| 4,992,998 A | | 2/1991 | Woodward | 367/99 |
| 5,022,266 A | | 6/1991 | Cody et al. | 73/579 |
| 5,022,268 A | | 6/1991 | Wolf et al. | 73/602 |
| 5,038,067 A | | 8/1991 | Tabin | 310/334 |
| 5,218,575 A | | 6/1993 | Cherek | 367/140 |
| 5,260,910 A | | 11/1993 | Panton | 367/99 |
| 5,337,289 A | | 8/1994 | Fasching et al. | 367/140 |
| 5,339,292 A | | 8/1994 | Brown et al. | 367/176 |
| 5,587,969 A | | 12/1996 | Kroemer et al. | 367/99 |
| 5,635,632 A | | 6/1997 | Fay et al. | 73/61.63 |
| 5,651,286 A | | 7/1997 | Champion et al. | 73/290 V |
| 5,741,971 A | * | 4/1998 | Lacy | 73/597 |
| 5,768,939 A | | 6/1998 | Quayle et al. | 73/290 V |
| 5,789,676 A | | 8/1998 | Fay et al. | 73/290 V |
| 5,793,705 A | * | 8/1998 | Gazis et al. | 367/98 |
| 5,822,275 A | | 10/1998 | Michalski | 367/99 |
| 5,987,994 A | * | 11/1999 | Maltby et al. | 73/646 |
| 6,008,662 A | * | 12/1999 | Newton et al. | 324/724 |
| 6,301,546 B1 | * | 10/2001 | Weinstein et al. | 702/23 |

OTHER PUBLICATIONS

S. Watano, T. Fukushima and K Miyanami, "Use of Ultrasonic Techniques for the Measurement and Control of Bed Height in Tumbling Fluidized Bed Granulation" Advanced Powder Technology, v5, issue 2, pp. 119–128, 1994.
Liang–Shih Fan and Chao Zhu "Principles of Gas–Solid Flows" Cambridge U Press 1999, pp. 400–401.

* cited by examiner

Primary Examiner—Hezron Williams
Assistant Examiner—Katina Wilson

(57) ABSTRACT

The dynamic fluidized-bed level in an olefin polymerization reactor is determined by radar or ultrasound waves. Echoes are processed to take into account the turbulence caused by bubbles, which can be as large as four meters in diameter, bursting on the surface, expelling resin particles into the freeboard above the dynamic fluidized-bed level.

20 Claims, 5 Drawing Sheets

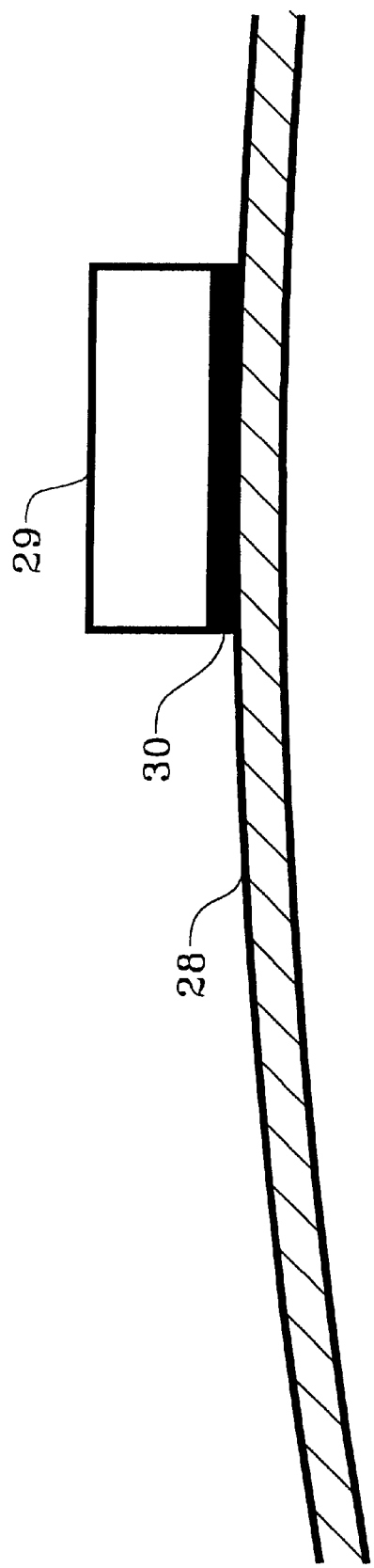

DETECTION OF DYNAMIC FLUIDIZED BED LEVEL IN A FLUIDIZED BED POLYMERIZATION REACTOR USING ULTRASONIC WAVES OR MICROWAVES

TECHNICAL FIELD

This invention uses ultrasonic waves or radar microwaves for detecting the dynamic fluidized bed level in a fluidized bed polymerization reactor.

BACKGROUND OF THE INVENTION

Many commonly used fluidized-bed reactors for olefin polymerization contain a dense "bed" in the reactor. The bed can be a gas-solid dense fluidized bed with or without the "condensing-mode" operation—that is, with or without the injection of liquid into the bed. Gas-phase polymerization reactors can be designed for either one-pass gas or for recycling of the gas. In either case, the location of bed level (or material level) in the reactor can be an important factor in the calculation and/or control of various limits of the process conducted in the reactor.

Usually in the past, the bed level of a fluidized bed in a fluidized-bed polyolefin reactor has been monitored by reading pressure differences among taps installed on the reactor wall. However, the taps can be easily blocked by particles, which causes a false bed-level reading. Also the bed-level measurement through pressure taps can be negatively affected by channeling and/or local defluidization in the reactor, particularly in some operations prone to local channeling, such as in the condensing mode and/or where there are sticky polymer particles. On occasion, the reactor is shut down due to problems in reading or controlling the bed level, even though the pressure taps may be blown free periodically.

Other commonly available methods for material level detection include invasive detectors which employ a simple probe inserted into the bed, and non-invasive radioactive detectors installed on the side of a reactor. Invasive probe detectors are vulnerable to fouling on the probe inserted into the bed. Radioactive detectors usually do not offer good accuracy and provoke environmental and safety concerns.

Fluidized beds, particularly the fluidized beds for large olefin polymerization reactors, present special problems for bed level measurement. Even in fluidized beds containing no liquid, bubbles are clearly present and discernable. The bubbles may vary in diameter from 0.05 meter to 4.0 meters, depending on the reactor's size and operating conditions. Bubbles are devoid of suspended particles, but significant quantities of particles are known to be ejected into the freeboard by bubbles in at least two ways—by ejection at the top surface of the bubble when it reaches the bed surface, and by expulsion from the wake of the bubble after it erupts through the surface of the bed. See "Principles of Gas-Solid Flows" by Liang-shih Fan and Chao Zhu, Cambridge Press (1988), page 401. Commonly the freeboard above the bed level will contain relatively coarse particles in its lower regions and finer ones higher up. In olefin polymerization, different types of polymers have different patterns of suspended density throughout the bed and above it. Because of the turmoil on the surface of the bed caused to a large extent by bursting bubbles, the bed level in a fluidized bed has been difficult to measure. We call such a bed level one characterized by substantially continuous bursting of bubbles of 0.05 to 4 meters in diameter—a dynamic bed level, or a dynamic fluidized-bed level.

U.S. Pat. No. 4,993,264 describes a method to use passive acoustics technology to monitor fluidized-bed level. A number of accelerometers were used on the side wall of a fluidized bed (not a polymerization reactor) to measure the wall vibration. By comparing the RMS acceleration from the accelerometers, the bed level can be defined. This technique requires several accelerometers and is more complicated than a single sensor or a single pair of sensors located on the top of the vessel. It is not practical for measuring dynamic bed level in a fluidized-bed polymerization reactor, as the wall is very thick and the mass of the polymerization reactor is very large. Moreover, the wall vibration is also affected by the way the fluidized-bed is mounted.

Ultrasonic waves and microwaves have been used in the past to measure various material and liquid levels in various containers and vessels. The principle is to put a transducer on the top of the vessel and transmit waves into the vessel. When the waves reach the material surface in the vessel, a part of the waves will be reflected back and received by the same or another transducer on top of the vessel. If the speed of the waves in the gas medium above the material level is known, the time difference between the wave transmitting and receiving can be used to calculate the location of bed level. However, these techniques have never been applied to polymerization reactors because of the special challenges mentioned above and the severe operational conditions of the reactor.

Satoro Watano et al in "The Use of Ultrasonic Techniques for the Measurement and Control of Bed Height in Tumbling Fluidized Bed Granulation," Advanced Powder Technology 5(2), 119–128 (1994) propose a technique of using ultrasonic waves to measure bed height in a tumbling fluidized bed. An ultrasonic transducer was used on top of the fluidized bed. Although it works successfully in a small size fluidized bed under ambient conditions with low gas velocity and a very small distance between bed level and the ultrasonic transducer (less than 300 mm), it can not be applied to polymerization reactors due to its limitation under high pressure, larger reactor size and the need to constantly calibrate the sound speed in the gas medium on top of the bed level.

SUMMARY OF THE INVENTION

The invention involves the use of ultrasonic transducer(s) or microwave transducer(s) installed on the top of the fluidized-bed polymerization reactor. The transducer transmits ultrasonic waves or microwaves as short pulses at predetermined frequencies and intensities and into the reactor freeboard. The waves reflected by the bed surface are received by the same transducer (transceiver) or by a separate wave receiver (transducer). The bed-level can be calculated from the travel time ("time of flight") of waves reflected by the bed surface. A signal processing unit is used to analyze the receiving signals and determine which of them from each pulse represents the bed level; the data are then processed to achieve a dynamic fluidized bed level.

A wave-speed model developed for high-pressure polymerization-reaction gas is associated with the signal processing unit to supply promptly a factor representing the effect of the instantaneous gas composition on the ultrasonic velocity. The transducer(s) can be installed either non-invasively on the exterior wall of the reactor, or through a port opened at the top of the reactor, preferably so that there is no projection into the reactor. Projection into the reactor, with contemporary technology, should be minimized, but if a way can be found to assure that the projection will not be fouled, or that if it is, the fouling will be obviated by the ultrasonic or microwave readings, such projections are contemplated within our invention.

In addition to being able to detect or measure dynamic bed level in spite of the complicating factors that contribute to it, a measurement system should be able to operate in a wide range of pressure and temperature conditions, it should not be vulnerable to fouling, it should be able to achieve an accurate measurement in spite of an irregular and constantly moving dynamic surface, it should be able to obviate any measurement interference from particles in the freeboard, it should distinguish the bed level from other surfaces in the environment, and it should be able to adjust its readout for continuous changes in gas composition, viscosity, superficial gas velocity, and other characteristics of the suspending medium.

The duration of the pulses may be from 1 millisecond (1 ms) to one second, and the pulse is repeated many times (e.g., 20 to 200 times) with short intervals between consecutive pulses to get an averaged reading of the bed level.

The bed-level detection system of the present invention can achieve prompt bed-level monitoring without the influence of tap plugging and fouling and is not affected by the local defluidization and/or channeling in the reactor. In addition, the environmental and safety problems associated with the nuclear bed-level detector are avoided.

Use of ultrasonic waves or microwaves allows the bed-level measurement to be independent of pressure taps.

BRIEF DESCRIPTION OF THE DRAWINGS

FIG. 2 shows the installation of the ultrasonic transducer of FIG. 1 on the wall of the expanded section.

DETAILED DESCRIPTION OF THE INVENTION

Figure 1A:
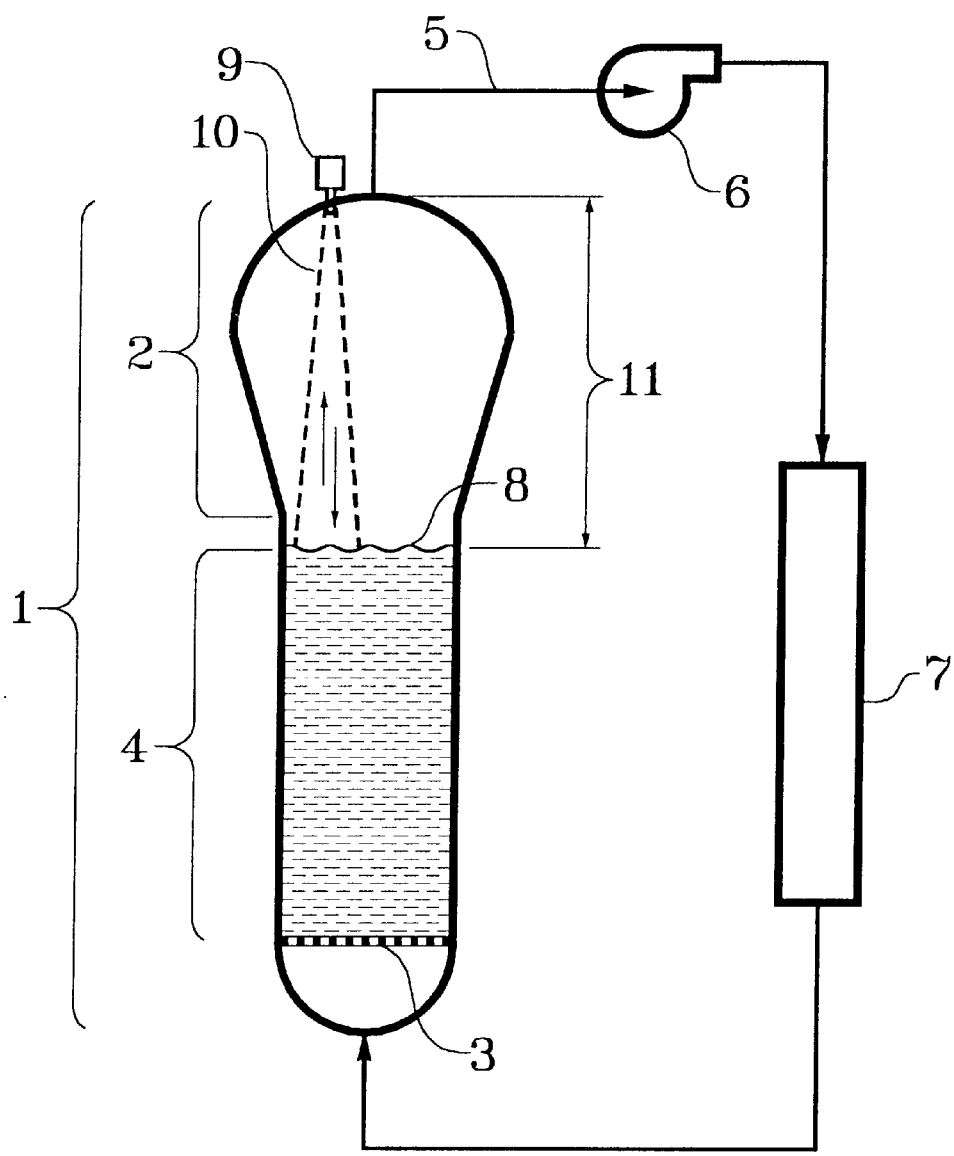
FIG. 1a is an idealized schematic of the installation of our system on an olefin polymerization reactor using a fluidized bed.

The present invention provides an innovative and simple method of dynamic bed-level detection in fluidized-bed polymerization reactors by ultrasonic waves or microwaves. The fluidized bed reactors can be mechanically stirred and/or gas fluidized, and can be operated under the "condensing-mode." This measurement technology is generally applicable to dynamic fluidized-bed levels in a wide range of polymerization systems using a wide range of catalysts.

The invention includes the use of at least one transducer installed on the top of the polymerization reactor for sending ultrasonic waves or microwaves into the reactor; the same transducer or another transducer on top of the reactor having means for receiving the waves reflected by the bed surface; and a processing unit which calculates the travel time of reflected waves taking into account (in the case of ultrasonic instrumentation) instantaneous variation of wave speed with the gas composition in the freeboard, and then calculates the location of bed level. We use the term transducer to include any device which converts electrical energy to sonic or radar waves, or converts sonic or radar waves to electrical signals. A transmitter transmits, a receiver receives, and a transceiver may do both in the context of our invention.

Ultrasonic transducers can be installed non-invasively on the outside surface of the reactor wall, or invasively on the reactor wall through a nozzle. For the invasive choice, the housing of the ultrasonic transducer should be designed to tolerate pressure up to 1000 psi and temperature up to 200° C. The operating frequency range of the ultrasonic detector is advantageously between 20 kHz and 600 MHz.

For the non-invasive ultrasonic detector, the frequency of the ultrasonic waves is selected to provide a wavelength of about 2.6 to about 8 times the metal reactor wall thickness and most preferably will be 3.2~5.3 times the wall thickness. Generally, the reflected signals will be reflected over a wider area even if the transmission focuses on a small area and the receiver will tend not to receive the full strength of the reflected signal; accordingly, we utilize a large area receiver. The non-invasive transducer requires a close contact with the reactor exterior wall and its diameter is preferably larger than about 7 times the wall thickness and most preferably larger than about 15 times the wall thickness, in order to assure that the receiver can pick up the reflected signals. Close contact with the wall may be assured by fixing the transducer to the wall with epoxy cement.

Microwave transducers (also called microwave antennas or transmitters or radar antennas or transmitters) can be installed through an opening on the top of the reactor, and is designed to hold pressure up to 1000 psi and temperature up to 200° C. The preferred frequency range for a microwave detector is between 4 GHz and 30 GHz and most preferably between 5 GHz and 25 GHz.

Polymers and Monomers

Illustrative of the polymers which can be produced in accordance with the invention are the following: homopolymers and copolymers of $C_2$–$C_{18}$ alpha olefins; polyvinyl chlorides, ethylene propylene rubbers (EPRs); ethylene-propylene diene rubbers (EPDMs); polyisoprene; polystyrene; polybutadiene; polymers of butadiene copolymerized with styrene; polymers of butadiene copolymerized with isoprene; polymers of butadiene copolymerized with acrylonitrile; polymers of isobutylene copolymerized with isoprene; ethylene butene rubbers and ethylene butene diene rubbers; polychloroprene; norbornene homopolymers and copolymers with one or more $C_2$–$C_{18}$ alpha olefin; terpolymers of one or more $C_2$–$C_{18}$ alpha olefins with a diene; and the like.

Monomers that can be employed in the process can include one or more: $C_2$ to $C_{18}$ alpha olefins such as ethylene, propylene, and optionally at least one diene (such as those taught in U.S. Pat. No. 5,317,036 to Brady et al.), for example, hexadiene, dicyclopentadiene, octadiene, norbornadiene, and ethylidene norbornene; readily condensable monomers such as those taught in U.S. Pat. No. 5,453,471 including isoprene, styrene, butadiene, isobutylene, chloroprene, acrylonitrile, cyclic olefins such norbornenes, and the like.

Polymerization Process

The process of the present invention can be used in conjunction with fluidized bed (including stirred and/or gas phase fluidized bed) polymerizations.

Preferably, the present invention is employed in fluidized polymerizations, most preferably gas phase fluidized bed reactors. The present invention is not limited to any specific type of fluidized or gas-phase polymerization reaction and can be carried out in a single reactor or multiple reactors (that is, two or more reactors in series). In addition to well known conventional gas-phase polymerizations processes, "condensed mode", including the so-called "induced condensed mode", and "liquid monomer" operation of a gas phase polymerization can be employed.

A conventional fluidized bed process for producing resins is practiced by passing a gaseous stream containing one or more monomers continuously through a fluidized-bed reactor under reactive conditions in the presence of at least one polymerization catalyst. Product is withdrawn from the reactor. A gaseous stream of unreacted monomer is withdrawn from the reactor continuously and recycled into the reactor along with make-up monomer added to the recycle stream. Conventional gas-phase polymerizations are disclosed, for example, in U.S. Pat. Nos. 3,922,322 and 4,035,560.

Condensed mode polymerizations are disclosed in U.S. Pat. Nos. 4,543,399; 4,588,790; 5,352,749; and 5,462,999. Condensing mode processes are employed to achieve higher cooling capacities and, hence, higher reactor productivity. In these polymerizations a recycle stream, or a portion thereof, can be cooled to a temperature below the dew point in a fluidized bed polymerization process, resulting in condensing all or a portion of the recycle stream. The recycle stream is returned to the reactor. The dew point of the recycle stream can be increased by increasing the operating pressure of the reaction/recycle system and/or increasing the percentage of condensable fluids and decreasing the percentage of non-condensable gases in the recycle stream. The condensable fluid may be inert to the catalyst, reactants and the polymer product produced; it may also include monomers and comonomers. The condensing fluid can be introduced into the reaction/recycle system at any point in the system. Condensable fluids include saturated or unsaturated hydrocarbons. In addition to condensable fluids of the polymerization process itself, other condensable fluids, inert to the polymerization can be introduce to "induce" condensing mode operation. Examples of suitable condensable fluids may be selected from liquid saturated hydrocarbons containing 2 to 8 carbon atoms (e.g., ethane, propane, n-butane, isobutane, n-pentane, isopentane, neopentane, n-hexane, isohexane, and other saturated $C_6$ hydrocarbons, n-heptane, n-octane and other saturated $C_7$ and $C_8$ hydrocarbons, and mixtures thereof). Condensable fluids may also include polymerizable condensable comonomers such as olefins, alpha-olefins, diolefins, diolefins containing at least one alpha olefin, and mixtures thereof In condensing mode, it is desirable that the liquid entering the fluidized bed is dispersed and vaporized quickly.

Liquid monomer polymerization mode is disclosed, in U.S. Pat. No. 5,453,471. When operating in the liquid monomer mode, liquid can be present throughout the entire polymer bed provided that the liquid monomer present in the bed is adsorbed on or absorbed in solid particulate matter present in the bed, such as polymer being produced or fluidization aids (e.g., carbon black) present in the bed, so long as there is no substantial amount of free liquid monomer present more than a short distance above the point of entry into the polymerization zone. Liquid mode makes it possible to produce polymers in a gas phase reactor using monomers having condensation temperatures much higher than the temperatures at which conventional polyolefins are produced. In general, a liquid monomer process is conducted in a stirred bed or gas fluidized bed reaction vessel having a polymerization zone containing a bed of growing polymer particles. The process comprises continuously introducing a stream of one or more monomers and optionally one or more inert gases or liquids into the polymerization zone; continuously or intermittently introducing a polymerization catalyst into the polymerization zone; continuously or intermittently withdrawing polymer product from the polymerization zone; and continuously withdrawing unreacted gases from the zone; compressing and cooling the gases while maintaining the temperature within the zone below the dew point of at least one monomer present in the zone. If there is only one monomer present in the gas-liquid stream, there is also present at least one inert gas. Typically, the temperature within the zone and the velocity of gases passing through the zone are such that essentially most liquid presented in the polymerization zone is adsorbed on or absorbed in solid particulate matter.

Typically, the fluidized bed polymerization process is conducted at a pressure ranging from about 10 to 1000 psi, preferably about 200 to about 600 psi and a temperature ranging from about 10° C. to about 150° C., preferably about 40° C. to about 125° C. During the polymerization process the superficial gas velocity ranges from about 0.3 to 3.5 feet/second, and preferably about 0.7 to 2.7 feet/second. A microwave bed-level measurement device which will withstand the above described conditions is made by TN Technologies Inc. of Texas.

Additionally, the polymerization process of the present invention can include other additives such as inert particles. Inert particles can include, for example, carbon black, silica, clay, and talc used in some processes which produce sticky polymers. The various compositions of the resin particles, which may include carbon, silica, and other materials incorporated in them, do not significantly affect the process.

FIG. 1a is a simplified diagram of a typical gas-phase fluidized-bed olefin polymerization reactor. The reactor has a straight cylindrical section 1 and an expanded section 2. Gas, comprising essentially olefin monomer, is introduced from the bottom through a distributor plate 3. Polymer particles are formed from the monomer in the presence of catalyst introduced through ports not shown, and the polymer particles form a dense fluidized bed 4 suspended in the rising gas. The particles are removed by pressure difference as is known in the art (see, for example, Aronson U.S. Pat. No. 4,621,952) through a duct and product withdrawal system not shown, usually located at a lower or midpoint level in the fluidized-bed 4. The gas is recycled through recycle pipe 5, compressed at compressor 6 and cooled in cooler 7 to remove the heat of reaction in order to control the temperature in the reactor and enhance the process efficiency as is known in the art. The purpose of the expanded section 2 is to reduce the gas velocity in the higher regions of the reactor to help the particles remain in the bed. The region above the dense bed 4, generally including all the volume of the expanded section 2, is sometimes known as the freeboard area. It may contain some particles, or "dust" but is generally a dilute phase system with a quite small concentration of particles, i.e. at least one order of magnitude below that of the dense bed. See the further explanation below with respect to FIGS. 1b and 1c. Depending on the numerous variables and conditions possible in such a reactor, the bed level 8 may be smooth or "wavy", as shown, and/or may be somewhat distended into the expanded section 2. But almost all such fluidized bed levels are dynamic, continuously subject to the eruption of bubbles. Fines are present directly above the bed level 8. The fines concentration decreases sharply with increasing height because of gravity, and reaches a stable level above the Transport Disengagement Height ("TDH"), which is defined as the level above which no particles will return to the bed by gravity. All suspended particles above the TDH will be carried over by the rising gas. Although there may be fines in the freeboard, there are fundamental differences between the dense bed and the freeboard, namely (1) in freeboard, the particle phase is the discrete phase and gas phase is the continuous phase; while in the dense bed, particle phase (or the emulsion phase) may be considered the continuous phase and the gas bubble phase is the discrete phase. There are no bubbles above the dense bed surface, and (2) there is a significant difference in particle concentration below and above the bed surface. Below the bed surface, the volumetric particle concentration is in the order of 30–60%, while the typical particle concentration in the freeboard is generally no more than a few percent by volume and more typically far less than that. See Fan and Zhu, "Principles of Gas-Solid Flows", Cambridge press 1998, p 400–401.

FIG. 1a shows an ultrasonic transmitter 9 mounted on the outside of the upper wall of the expanded section 2. It directs ultrasonic waves 10 toward the bed surface 8 of the fluidized bed 4, and also receives the reflections of the waves. Ultrasonic waves 10 are shown in a focused or projected pattern of about a five degree angle; while a relatively small angle such as five degrees is preferred, it is not essential, and in fact the focus of either ultrasound or radar waves can be as small as one degree or less, or may cover the entire upper surface of the fluidized-bed 4.

Figure 1C:
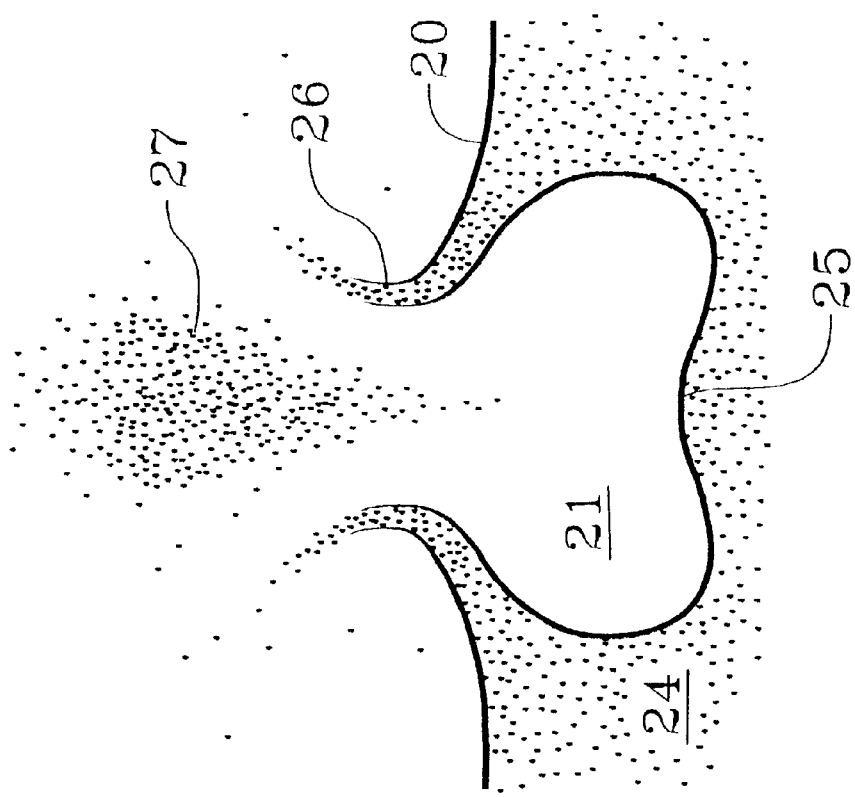
FIGS. 1b and 1c are reproduced from the Fan and Zhou reference cited elsewhere herein and illustrate the eruption of bubbles at a dynamic fluidized bed level.
Figure 1B:
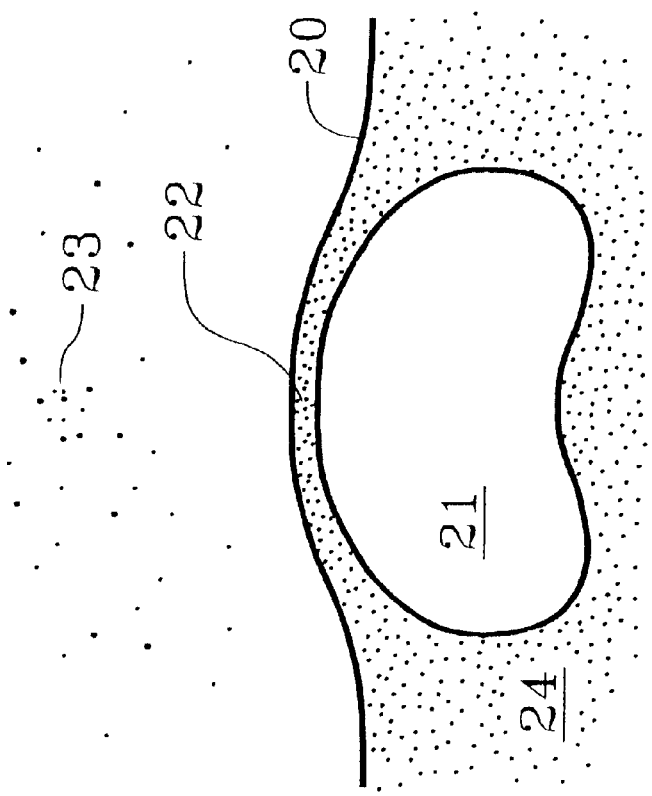

In FIGS. 1b and 1c, the principal sources and causes of turbulence at the fluidized-bed level are illustrated. As mentioned previously, the fluidized-bed 24 of resin particles is supported by a gaseous medium rising from distributor plate 3 near the bottom of the reactor. Bubbles such as bubble 21 rise rapidly in the medium of the fluidized-bed 24 as a function of the superficial gas velocity (SGV) and may assume various shapes and sizes depending on their position and velocity as well as other variables of the fluidized-bed 24. They may vary in diameter from 0.05 to 4.0 meters, more commonly 0.5 to 3.5 meters. As illustrative bubble 21 approaches surface 20 of the fluidized-bed, bubble roof 22 becomes distended and particles 23 are ejected as the bubble roof 22 disintegrates. In FIG. 1c, the ejected particles 27 are derived not only from roof 22 but also from the bubble wake 25 as the collapsing sides 26 move outwardly and wake 25 rises.

FIG. 2 shows the ultrasonic transmitter of FIG. 1 installed on the top of upper wall 28 of the expanded section 2. Upper wall 28 is slightly curved and accordingly it is usually desirable to affix the ultrasonic transmitter 29 to wall 28 with cement 30 to provide a continuous solid interface between wall 28 and transmitter 29. Transmitter 29 receives as well as transmits the ultrasonic waves, and, as described elsewhere herein, preferably has a relatively large area of contact with the wall 28 in order to detect reflections which may be diminished in strength over a large area.

Figure 3:
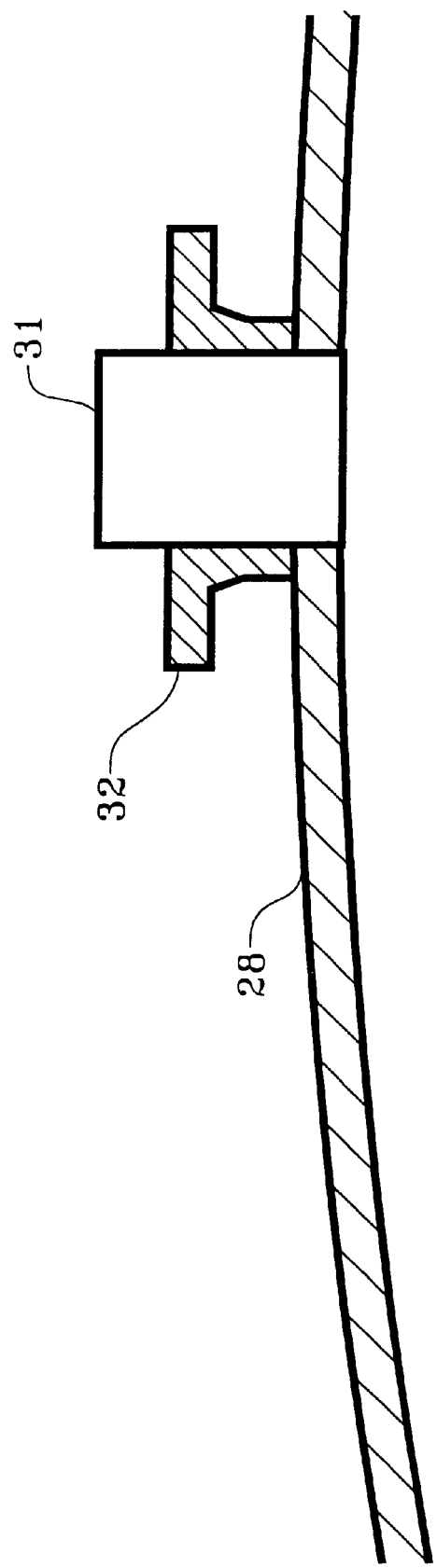
FIG. 3 is a sectional view of an intrusive microwave transducer fixed in intimate contact with the exterior of the wall of the expanded section 2.

FIG. 3 is a semi-sectional view of an intrusive microwave transceiver 31 fixed in intimate contact with, and passing through, the exterior of the wall 28 of the expanded section 2. We call this configuration intrusive because a port 32 is placed in wall 28 to provide an entrance for the transceiver 31. Transceiver 31 is thus able to transmit radar waves directly into expanded section 2 without having to transmit it through the usually rather thick steel wall 28.

Figure 4:
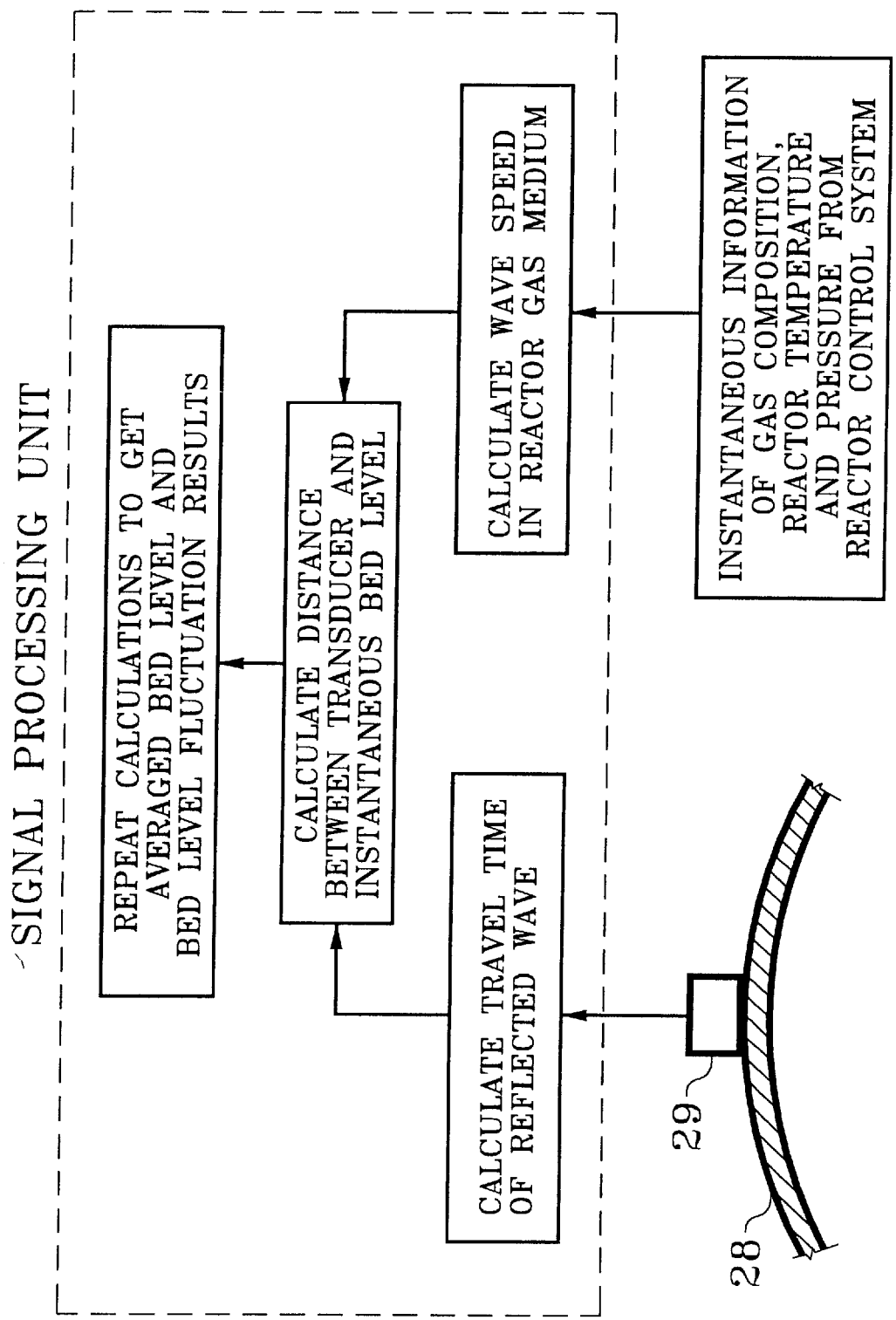
FIG. 4 shows the computer and software functions of the system in diagrammatic form.

FIG. 4 summarizes the alternative invasive or non-invasive processing of the signals. Microwave or ultrasonic transmitter 29 located on top wall 28 transmits and receives the wave energy and relays a signal representing what it receives to the devices within the dotted line, which perform the steps spelled out in FIG. 4. Outside the dotted line, for an ultrasound system, an additional input of information on gas composition, reactor temperature and/or pressure is introduced to the calculations to account for distortions or variations in the speed of sound waves in the fluidized-bed, and the output at the top of the diagram is modified accordingly.

Statistically, the time averaged fluidized-bed level at one location is equal to the time-averaged overall bed level for the whole cross-sectional area of the bed. Therefore, we may transmit the waves to a particular area or locale on the bed surface. Each calculated data point of bed level is the averaging result of many sonic or radar measurements (e.g. 20–200 measurements). Each measurement includes (a) transmitting the wave toward the bed for a very short time such as 1 millisecond to 1 second (that is, the waves are sent in pulses), receiving the reflected pulse, and calculating the waves' travel time and the instantaneous wave speed in freeboard. For determining the speed of ultrasonic waves, factors should be included for the instantaneous gas composition and operating pressure and temperature. Such measurements are repeated many times (e.g. 20–200 times) with very short intervals between measurements (e.g., 5 ms to 1 s) to get an averaged bed level reading. As a practical matter, where the pulses are very short and the time between them is similarly short, the wave speed calculation may be performed for only some of the measurements, instead of at each measurement repeatedly, because variations in gas composition and reactor operating conditions usually require some time to acquire significance. Any statistically sound number of measurements may be used. In addition, by monitoring deviations of measurements from the averaged bed level, the magnitude of dynamic bed level fluctuation can be determined. The magnitude of bed level fluctuation can be determined over longer periods of time ((for example, two minutes or more)) and used as an indicator of normal or abnormal reactor operation.

If the fines concentration in the freeboard is significant enough to block the wave energy reflections, or the measurement system is set improperly, to the extent that at least 0.01% of the emitted wave energy is not received, the system will not perform satisfactorily.

The measurement system of this invention is not significantly affected by particle size or density of the particles.

Catalysts

Any type of polymerization catalyst may be used in the polymerization process of the present invention. A single catalyst may be used, or a mixture of catalysts may be employed, if desired. The catalyst can be soluble, or insoluble, supported or unsupported. It may be a prepolymer, spray dried with or without a filler, a liquid, or a solution, slurry or dispersion. These catalysts are used with cocatalysts and promoters well known in the art. Typically these are aluminum-alkyls, halides, as hydrides and well as aluminoxanes. For illustrative purposes only, examples of suitable catalysts include:

A. Ziegler-Natta catalysts, including titanium based catalysts such as those described in U.S. Pat. Nos. 4,376, 062 and 4,379,758. Ziegler-Natta catalysts are well known in the art, and typically are magnesium/titanium/electron donor complexes used in conjunction with an organoaluminum cocatalyst.

B. Chromium based catalysts such as those described in U.S. Pat. Nos. 3,709,853; 3,709,954; and 4,077,904.

C. Vanadium based catalysts such as vanadium oxychloride and vanadium acetylacetonate, such as described in U.S. Pat. No. 5,317,036.

D. Metallocene catalysts and other single-site or single-site-like catalysts such as those taught in U.S. Pat. Nos. 4,530,914; 4,665,047; 4,752,597; 5,218,071; 5,272, 236; 5,278,272; 5,317,036; and 5,527,752.

E. Cationic forms of metal halides, such as aluminum trihalides.

F. Anionic Initiators such as butyl lithiums.

G. Cobalt catalysts and mixtures thereof such as those described in U.S. Pat. Nos. 4,472,559 and 4,182,814.

H. Nickel catalysts and mixtures thereof such as those described in U.S. Pat. Nos. 4,155,880 and 4,102,817.

I. Rare earth metal catalysts, i.e., those containing a metal having an atomic number in the Periodic Table of 57 to 103, such as compounds of cerium, lanthanum, praseodymium, gadolinium and neodymium. Especially useful are carboxylates, alcoholates, acetylacetonates, halides (including ether and alcohol complexes of neodymium trichloride), and allyl derivatives of such metals, e.g., of neodymium. Neodymium compounds, particularly neodymium neodecanoate, octanoate, and versatate, and n-alkyl neodymium are the most preferred rare earth metal catalysts. Rare earth catalysts are especially preferred and used to produce polymers polymerized using butadiene, styrene, or isoprene and the like.

Preferred catalysts for the process of the present invention include rare earth metal catalysts, titanium catalysts, vanadium catalysts, and the metallocene/single-site/single-site-like catalysts.

Bed Level Detection Devices

Accordingly, the present invention provides an innovative and simple method of dynamic fluidized-bed level detection in polymerization reactors by ultrasonic waves or microwaves. The invention includes 1) at least one transducer installed on the top of the polymerization reactor, sending ultrasonic waves or microwaves into the reactor; and 2) the same transducer or another transducer on top of the reactor, receiving the waves bounced-back by the bed level; and 3) a single processing unit which calculates the travel time of bounced-back waves in the reactor freeboard, and calculates the wave speed based on the instantaneous gas composition in the freeboard, and reactor operating conditions, and then calculates the location of bed level.

A model specially developed for wave-speed calculation in high-pressure hydrocarbon gas medium is employed by the data processing unit.

Ultrasonic transducers can be installed non-invasively on the outside surface of the reactor wall, or invasively on the reactor wall through a nozzle. For the invasive choice, the housing of the ultrasonic transducer is designed to hold pressure up to 1000 psi and temperature up to 200° C. The operating frequency range of the ultrasonic detector is between 20 kHz and 600 MHz.

For the non-invasive ultrasonic detector, the frequency of the ultrasonic waves is selected to make the reactor wall thickness be preferably ⅛~⅜ of the wavelength in the wall material (usually steel) and most preferably be 3/16~5/16 of the wavelength in the wall. The non-invasive transducer requires a close contact with the reactor exterior wall and its diameter is preferably larger than about 7 times of the wall thickness and most preferably larger than about 15 times of the wall thickness. The diameter requirement is to reduce the diffraction loss of the reflected waves to an acceptable level.

Microwave transducers (antennas) can be installed through a nozzle opened on the top of the reactor, and is designed to have the mechanical strength to stand (for example, model RCM of TN Technologies, Inc.) pressures up to 1000 psi and temperature up to 200° C. Preferably the microwave transducer will be placed inside the reactor but will not protrude from the internal wall surface. The preferred frequency range for microwave detector is between 4 GHz and 30 GHz and most preferably between 5 GHz and 25 GHz.

The bed-level detection system should be able to perform its task of calculating the dynamic fluidized-bed level using directly reflected energy as little as 1/10,000 of the sending wave energy. Such a feature is important to measure the dusty and wavy bed level in fluidized-bed polymerization reactors.

For a "dusty" bed level in gas-solid fluidized-bed polymerization reactor, the ultrasonic detector is preferred over the microwave detector since the relatively low wavelength can penetrate deep and better handle the dust effect. On the other hand, a microwave detector is preferred for reactors with lesser amounts of dust in the freeboard, and reactors with less freeboard height or volume since the instant wave-speed calibration (taking into account the composition, temperature and pressure of the gas medium in the freeboard space) is not needed for the microwave detector and the data processing unit associated with the detector can be simplified.

For most gas-solid fluidized-bed polymerization reactors, the ultrasonic detector is preferred over the microwave detector, because the relatively low dielectric coefficient of the polymer would make a relatively weak reflection of microwaves by the bed surface.

For a reactor with relatively long distance from the bed surface to the top of the reactor, the ultrasonic detector is also preferred over the microwave detector, since the microwaves attenuate faster than ultrasonic waves do.

For reactor with strong fouling possibility on the wall, the microwave detector is preferred over the ultrasonic detector, since the measurement accuracy of the former is even less affected by the wall fouling.

EXAMPLE

A large commercial gas-solid fluidized-bed reactor having a configuration as shown in FIG. 1 is used to produce polyethylene. The wall thickness on the top of the reactor is 1–7/16 inches. An ultrasonic transducer with a diameter of 16 inches is attached on the top of the reactor non-invasively. The ultrasonic frequency is selected as 35,000 Hz, which makes the quarter-wavelength be close to the wall thickness. The time-average power of the transducer is about 100 watts. The transducer is closely contacted with the external surface of the reactor wall. Ethylene-butene copolymers are made in the reactor.

Detail of the reactor operating conditions and product properties are listed as the following table:

| | |
|---|---|
| Resin Density (g/cc) | 0.918 |
| Resin Melt Index (dg/10 min.) | 1.00 |
| Reactor Temperature (° C.) | 88 |
| Reactor Pressure (psig) | 305–309 |
| Ethylene Partial Pressure (psi) | 118–122 |
| Hydrogen/Ethylene Mole Ratio | 0.123–0.127 |
| Butene/Ethylene Mole Ratio | 0.356–0.360 |
| Production Rate (lb/hr) | 38,000 |
| Space-Time-Yield (lb/hr–ft$^3$) | 9.4 |
| Weight-Averaged Particle Size (in.) | 0.04 |
| Particle Settled Bulk Density (lb/ft$^3$) | 22 |
| Catalyst | Titanium based catalyst |
| Catalyst Support | Silica |
| Superficial Gas Velocity (ft/s) | 2.40 |

An independent bed-level measurement system through pressure difference is also installed, with all the pressure taps cleaned before the reactor start-up and blown by nitrogen during the operation. The gas composition constantly changes in a small range during the reactor operation. The speed of ultrasonic waves is promptly calculated by the data processing unit, following the variation of gas composition. The ultrasonic bed-level detector successfully monitors the fluctuation of bed level (about ±1.5 ft) and gets a good agreement with the results of pressure difference measurement. Operation and readings from the ultrasonic bed level detector are generally stable throughout an entire month. However, toward the end of the month, the pressure taps begin to report a bed-level reading lower than that detected by the ultrasonic detector. Drilling the pressure taps found that one of the pressure taps is partially plugged. And the pressure difference measurement gets a bed level close to what measured by ultrasonic detector after drilling the pressure taps.

What is claimed is:

1. Method of measuring a dynamic fluidized-bed level in a fluidized-bed olefin polymerization reactor, said reactor having a top wall and said fluidized bed having a superficial gas velocity of 0.3 to 3.5 feet per second and including bubbles bursting at said fluidized-bed level, said bubbles having an average diameter of 0.05 meter to 4 meters, comprising transmitting a series of short pulses of ultrasonic waves or microwaves from said top wall toward said fluidized-bed, receiving from said fluidized-bed level reflections of at least 0.01% of said ultrasonic or microwave pulses, calculating the times between said transmission and reception of said pulses, and calculating said bed level from said times.

2. Method of claim 1 wherein said transmitting and said receiving are performed by the same instrument.

3. Method of claim 1 wherein said waves are ultrasonic and said transmitting and receiving are performed on the exterior of said top wall.

4. Method of claim 3 wherein said waves are ultrasonic waves having a wavelength from 2.6 to 8 times the thickness of said top wall.

5. Method of claim 3 wherein said receiving takes place over an area on said top wall having a diameter 7 to 15 times the thickness of said top wall.

6. Method of claim 1 wherein said pulses are ultrasonic, and said calculating of said bed level includes a factor representing at least one of the composition, temperature and pressure of said fluidized-bed.

7. Method of claim 1 wherein each of said pulses has a duration from one millisecond to one second and from 10 to 500 pulses are transmitted at intervals from 2 milliseconds to 10 seconds.

8. Method of claim 1 wherein said waves are ultrasonic waves having a frequency of from 20 kHz to 10 MHz.

9. Method of claim 1 wherein said waves are microwaves at a frequency from 4 to 30 GHz.

10. Method of claim 1 wherein said waves are microwaves at a frequency between 5 and 25 GHz.

11. Method of claim 1 including the step of determining which of said at least 0.01% of said received waves is received from said dynamic fluidized bed surface.

12. Method of monitoring dynamic fluidized-bed level in a fluidized-bed olefin polymerization reactor having a top wall comprising fixing an ultrasonic transceiver to the exterior of said top wall, emitting ultrasonic waves having wavelengths of about 2.8 to about 8 times the thickness of said top wall from said transducer through said top wall and toward said dynamic fluidized-bed level, receiving ultrasonic waves reflected from said dynamic fluidized-bed level in a receiver having a diameter about 7 to about 15 times the thickness of said top-wall, and computing said bed level from the difference in time between said emission and said reception of said ultrasonic waves.

13. Method of claim 12 wherein said computing includes a factor representing at least one of temperature, pressure or temperature of the gaseous atmosphere in said reactor.

14. Method of claim 12 wherein 20 to 200 pulses are transmitted.

15. Method of claim 12 wherein said computing includes a factor representing superficial gas velocity in the reactor.

16. Method of claim 12 wherein said dynamic fluidized bed level is characterized by the substantially continuous bursting of bubbles of 0.05 to 4 meters in diameter.

17. Method of determining a magnitude of fluctuation of a dynamic fluidized-bed level comprising receiving reflections of waves emitted from a wave transmitter to said dynamic fluidized-bed level, calculating one or more averages of at least one characteristic of said reflections, and analyzing deviations from said average or averages to determine said magnitude of fluctuation.

18. Method of claim 17 including the step of comparing a statistical analysis of said deviations to a base representing a normal dynamic fluidized bed.

19. Method of claim 18 wherein said dynamic fluidized-bed level is characterized by the substantially continuous bursting of bubbles of 0.05 to 4.0 meters in diameter.

20. Method of claim 17 wherein said dynamic fluidized-bed level is characterized by the substantially continuous bursting of bubbles of 0.05 to 4.0 meters in diameter.

* * * * *